(12) United States Patent
Egloff

(10) Patent No.: US 12,042,637 B2
(45) Date of Patent: Jul. 23, 2024

(54) DEVICE AND METHOD FOR DISPENSING AT LEAST ONE SUBSTANCE

(71) Applicant: SHL MEDICAL AG, Zug (CH)

(72) Inventor: Christoph Egloff, Neuhausen am Rheinfall (CH)

(73) Assignee: SHL Medical AG, Zug (CH)

( * ) Notice: Subject to any disclaimer, the term of this patent is extended or adjusted under 35 U.S.C. 154(b) by 906 days.

(21) Appl. No.: 17/056,703

(22) PCT Filed: May 28, 2019

(86) PCT No.: PCT/EP2019/063710
§ 371 (c)(1),
(2) Date: Nov. 18, 2020

(87) PCT Pub. No.: WO2019/229010
PCT Pub. Date: Dec. 5, 2019

(65) Prior Publication Data
US 2021/0205538 A1     Jul. 8, 2021

(30) Foreign Application Priority Data
May 29, 2018   (EP) ..................................... 18174940

(51) Int. Cl.
*A61M 5/20*     (2006.01)
*A61M 5/31*     (2006.01)
*A61M 5/315*    (2006.01)

(52) U.S. Cl.
CPC ........ *A61M 5/2066* (2013.01); *A61M 5/2033* (2013.01); *A61M 5/31511* (2013.01); *A61M 2005/3128* (2013.01)

(58) Field of Classification Search
CPC .............. A61M 5/2066; A61M 5/2033; A61M 5/31511; A61M 2005/3128;
(Continued)

(56) References Cited

U.S. PATENT DOCUMENTS

| 5,298,023 A | 3/1994 | Haber et al. |
| 2014/0049041 A1 | 2/2014 | Eggert et al. |
| 2017/0136183 A1 | 5/2017 | Helmer |

FOREIGN PATENT DOCUMENTS

| JP | S61-502865 A | 12/1986 |
| JP | H07-501234 A | 2/1995 |

(Continued)

OTHER PUBLICATIONS

International Search Report and Written Opinion for Int. App. No. PCT/EP2019/063710, mailed Jul. 24, 2019.

*Primary Examiner* — Robert J Utama
*Assistant Examiner* — Neeraja Gollamudi
(74) *Attorney, Agent, or Firm* — McDonnell Boehnen Hulbert & Berghoff LLP

(57) ABSTRACT

A device and a method for dispensing at least one substance to a patient is presented where the device has a movable first container containing a first substance having a first piston with a first piston rod, a movable second container containing a second substance having a second piston with a second piston rod, an injection device, and a conduit device for guiding the contents of the second container to the first container and the contents of the first container to the injection device, wherein the first and the second piston are each movable via at least one pre-tensioned spring element. A free end of the first piston rod and a free end of the second piston rod are releasably held by a common holding component, and the common holding component is designed in such a way that a movement of the common holding component results in a successive release of the first piston rod and the second piston rod.

24 Claims, 8 Drawing Sheets

(58) Field of Classification Search
CPC .............. A61M 2005/247; A61M 5/19; A61M 5/2448; A61M 2005/1787; A61M 5/1407; A61M 5/1408; A61M 5/1409; A61M 5/284; A61M 5/31596; A61M 5/3294
See application file for complete search history.

(56) References Cited

FOREIGN PATENT DOCUMENTS

| WO | 86/01120 A1 | 2/1986 |
|---|---|---|
| WO | WO8606965 * | 5/1986 |
| WO | 86/06965 A1 | 12/1986 |
| WO | 93/02720 A1 | 2/1993 |
| WO | 2017/085538 A1 | 5/2017 |
| WO | 2017/211851 A2 | 12/2017 |

* cited by examiner

DEVICE AND METHOD FOR DISPENSING AT LEAST ONE SUBSTANCE

CROSS REFERENCE TO RELATED APPLICATIONS

The present application is a U.S. National Phase Application pursuant to 35 U.S.C. § 371 of International Application No. PCT/EP2019/063710 filed May 28, 2019, which claims priority to European Patent Application No. 18174940.9 filed May 29, 2018. The entire disclosure contents of these applications are herewith incorporated by reference into the present application.

TECHNICAL AREA

The present disclosure relates to a device and a method for dispensing at least one substance, in particular to a patient. More precisely, the present disclosure relates in particular to a device and a method for the autoinjection of at least one substance by the user himself, i.e. usually by the patient, wherein the device according to the disclosure can also be referred to as an autoinjector and the method according to the disclosure can also be referred to as an autoinjection by means of the device according to the disclosure, i.e. by means of the autoinjector. An autoinjector here usually corresponds to a medical instrument which is used to administer a medical substance, which is generally in a liquid formulation/administration form, by parenteral injection. Autoinjectors are conventionally used in a treatment by injection of the medicinal substance in circumstances in which the injection of a pharmaceutically active agent is desired even in the absence of a physician or other health professional, for example in emergency situations in which the active agent to be injected should be administered as quickly as possible. When using an autoinjector, the injection usually performed by the user/patient himself, but can also be done by a third party, for example, in the event that the patient himself is no longer in a position to apply the autoinjector to himself.

BACKGROUND

When administering liquid formulations of medicinal substances or active pharmaceutical agents, it is necessary in most cases to deliver well-defined amounts of substance to a patient. Often these substances, usually medications, have to be injected into the body of the patient. Injection syringes, medication pens (so-called pens), or medication pumps are usually used for parenteral injection. However, there are also many emergency situations in which it is desirable to treat a patient with a liquid medicament or a liquid active agent solution. Even if the circumstances in such a situation make it impossible to carry out an intravenous injection, it can be essential to administer an active agent solution by injection as quickly as possible. However, the various substances that are to be injected depending on the type of emergency usually differ significantly from one another. For example, commercially available insulin can be stored already in liquid form for a long time, carried by the user, and then injected directly into the body if necessary without any preparation worth mentioning, whereas with preparations that are not stored in liquid form for a long period of time, increased requirements can be placed before or during the administration. In particular, biotechnologically produced active agents can often only be kept in freeze-dried or lyophilized form over a longer period of time, but due to their mostly powdery solid form, they cannot be administered by parenteral injection, but have to be brought into an injectable liquid form before administration. Lyophilizates of this type are only dissolved in an injection solution, for example an aqueous saline solution, shortly before they are administered, and then, for example, drawn into a syringe and subsequently injected. However, such a procedure can also be necessary for preparations that require two liquids to be mixed. In an emergency application, however, there is usually the problem that the user is either already in a state of shock or must not lose much time in order to administer the active agent. Accordingly, preparing the injection solution with the lyophilizate by hand, then drawing up the solution using a syringe, and then injecting the solution can take too long or require too complex actions that ultimately stand in the way of the injection with the often vital active agent.

As a solution to the above problem, automatic injection devices or autoinjectors have been used for a long time, which are usually safely stored before use and can be carried with them by the user/patient, are usually safe and easy to use and usually contain the correct dose of the substance to be injected in liquid formulation for the respective emergency or adapted to the respective clinical picture of the user. Thus, for example, WO 1986/006965 A1 describes an automatic injection device, using which a patient can reconstitute and administer a lyophilizate himself. The mode of operation of the injection device described therein is such that a diluent is mixed with a dry medicament component by a predetermined manual actuation procedure and then a second manual actuation procedure has to be carried out so that an injection needle is inserted into the muscle tissue of the patient and the liquefied medicament is injected by the injection needle into the muscle tissue. An embodiment described therein shows in particular an arrangement of two carpules having respective spring-actuated stoppers, wherein by turning a safety key and additionally releasing a first pin, the stopper of the first carpule conveys a liquid into the other carpule, in which the liquid is then mixed with the lyophilizate by shaking. By releasing a second pin, the stopper of the second carpule is then moved by the spring and the mixture or the solution of liquid and lyophilizate is thereby dispensed through the injection needle, which is exposed by the same actuating action. The injection device with two separate carpules described here has, inter alia, the decisive disadvantage, however, that the two carpules are essentially already connected to one another and thus a sterile transport of the lyophilizate within the injection device is no longer provided. In addition, the two carpules cannot be exchanged or replaced separately from one another before the injection device is used while maintaining the sterility of the respective carpule contents. If the shelf life of either the lyophilizate or the diluent has expired, in the described injection device, this accordingly results in a complete replacement of the entire injection device.

In view of the above-mentioned problems of the known prior art, it is therefore the object of the present disclosure to provide a device and a corresponding method for dispensing at least one substance, which overcome the disadvantages of the known prior art, preferably with simplified handling. This relates in particular to automatic mixing of two substances that are in two different containers while maintaining their respective sterility. However, depending on the embodiment, the overall manageability of the device during the autoinjection of the substance should also be simplified, with the autoinjection being made more painless, gentler, and safer by the combined triggering of various piston springs.

SUMMARY

The above-mentioned problems of the prior art are solved according to the present disclosure by means of a device for dispensing a substance and by means of a corresponding method as described in the appended claims.

More precisely, the present disclosure provides a device for dispensing at least one substance, wherein the substance to be dispensed consists of a mixture of two other substances, namely a first substance which contains at least one pharmaceutically active agent and a second substance which is in liquid form and forms an injectable substance after mixing with the first substance.

The first substance can be a pure pharmaceutically active agent or a mixture of a pure pharmaceutically active agent and one or more other chemical (especially pharmaceutically acceptable) compounds, wherein the first substance can be in liquid or solid form. The first substance is preferably in solid form, in particular in amorphous form. A lyophilizate is particularly preferred. The first substance can optionally contain one or more further pharmaceutically active agents. It is preferred that the first substance does not contain any further pharmaceutically active agent.

The second substance can be a liquid that consists of only one (in particular pharmaceutically acceptable) chemical compound, or a liquid or an emulsion that consists of a mixture of two or more (in particular pharmaceutically acceptable) chemical compounds, such as in particular a solution, for example an aqueous saline solution or the like. If the second substance is a liquid, the second substance is also referred to as a solution liquid. A reconstitution solution for dissolving a lyophilizate is particularly preferred. The second substance can optionally contain one or more further pharmaceutically active agents. It is preferred that the second substance does not contain any further pharmaceutically active agent.

The substance to be dispensed resulting from mixing the first and the second substance can be a liquid or an emulsion, in particular a solution.

The substance to be dispensed is preferably dispensed in an automatic manner in the sense of an autoinjector, and takes place in particular to a patient, such as the user of the device according to the disclosure. For this purpose, the device according to the disclosure has a first container which contains a first substance and which is provided with a first piston having a so-called first piston rod connected to it, wherein the first container is movably arranged in the device, i.e. can move inside the device in at least its longitudinal direction or along its longitudinal axis. The first piston and the first piston rod are preferably formed in one piece. The device according to the disclosure also comprises a second container which contains a second substance and is provided with a second piston having a so-called second piston rod connected thereto, wherein the second container is also movably arranged in the device, therefore can also move within the device at least in its longitudinal direction or along its longitudinal axis. The second piston and the second piston rod are preferably formed in one piece. The preferably cylindrical containers can be movably guided within the device, for example by guide rails or guide walls in the device in the respective container longitudinal direction, i.e. along the axial extension of each container, wherein the device correspondingly restricts a maximum axial movement of each container. To prevent mutual interference of the containers in their movement, the two containers can be arranged substantially in parallel, and in particular in the same direction, with respect to one another in the device. This configuration of the device allows diverse possibilities in the type of the second container and in the positioning thereof relative to the first container, whereby a compact and ergonomic device can be provided in comparison to the known prior art, which offers better manageability and is easier for the patient to carry with him. The first and the second container can be a standard carpule or a vial. Such containers are established in the prior art and meet the regulatory requirements, particularly in the case of pharmaceuticals, which are usually subject to an approval and registration process.

The device according to the disclosure also has an injection device which is used to ultimately inject the at least one substance, i.e. the contents of the two containers, into the patient, and a conduit device which, on the one hand, is provided to guide the contents of the second container to or into the first container, and on the other hand is also provided to guide the contents of the first container to or into the injection device. The injection device can be suitable for subcutaneous, intramuscular, intravenous, intraarterial, intraarticular, intracardiac, intracutaneous, intraosseous, intraperitoneal, intrapulmonary, intrathecal, intravitreal, or intrazolomatic (preferably for subcutaneous or intramuscular) dispensing. Subcutaneous dispensing is particularly preferred. The injection device can be a simple injection cannula or also a more complex structure, as is known, for example, from WO 2017/211851 A2, the content of which can be incorporated into the present description.

In the device according to the disclosure, the piston of the first container, i.e. the so-called first piston, and the piston of the second container, i.e. the so-called second piston, can each be moved via at least one pre-tensioned spring element after it has been triggered, i.e. the first piston of the first container can be moved by a so-called first spring element and the second piston of the second container by a so-called second spring element, as soon as the respective spring element is released and its pre-tension is accordingly converted into an expansion of the spring element. Each of the pre-tensioned spring elements can be provided in the form of a pre-tensioned spiral spring, the pre-tension of which is converted into an axial spring deflection of the respective spring element after it has been triggered. More precisely, the first spring element is directly in operative connection with the first piston or with the first container, and is guided via the first piston rod, wherein—if a spiral spring is used—for example, the first piston rod can be arranged inside the first spring element or the first spiral spring and thus maintains a pre-tension of the first spiral spring. A similar structure can be used in the second spring element. Providing such a pre-tensioned spring element or such pre-tensioned spring elements makes it possible, in a structurally simple manner, to effectuate an independent displacement of the respective piston or the respective container without a separate drive also being required for this purpose.

A free end of the first piston rod and a free end of the second piston rod are releasably held in the device according to the disclosure by a common holding component, wherein the common holding component is designed in such a way that a movement of the common holding component results in a successive release of the first piston rod and the second piston rod, thus first a release of the first piston rod and then a release of the second piston rod. This has the advantage that first the first piston is moved via the first piston rod and the first spring element in its longitudinal direction or along its longitudinal axis within the device, before then the second piston is moved via the second piston rod and the second spring element in its longitudinal direction or along its longitudinal axis within the device. According to a preferred embodiment of the present disclosure, a longitudinal axis of the common holding component is arranged essentially perpendicular to the longitudinal axes of the first and second piston rods, and a movement direction of the common holding component can extend substantially perpendicular to the movement directions of the two piston rods. Accordingly, the arrangement made up of the common holding component and the two piston rods in the device according to the disclosure is preferably designed so that a mechanical movement of the common holding component in its longitudinal direction results in a successive release of the first piston rod and the second piston rod, i.e. first a release of the first piston rod and a subsequent spring-induced movement of the first piston rod in its longitudinal direction or along its longitudinal axis, i.e. essentially perpendicular or essentially at right angles to the movement of the common holding component, and then a release of the second piston rod and a subsequent spring-induced movement of the second piston rod in its longitudinal direction or along its longitudinal axis, i.e. essentially perpendicular or essentially at right angles to the movement of the common holding component.

Due to the fact that both containers are movably arranged in the device, as explained above, it follows that a movement of the first piston triggered by the first spring element causes a movement of the first container within the device, and that a subsequent movement of the second piston triggered by the second spring element causes a subsequent movement of the second container within the device. Correspondingly, via the actuation of the common holding component, which can also be referred to as the trigger component or release component, and the subsequent release of the first piston rod and then the second piston rod resulting therefrom, first a movement of the first container following the spring force or the spring deflection of the first spring element and then a movement of the second container following the spring force or the spring deflection of the second spring element are induced. The common holding component is thus able to trigger successive movements of the two pistons of the device according to the disclosure, which are caused by the two pre-tensioned spring elements.

Accordingly, according to one preferred embodiment of the present disclosure, the common holding component holds the first piston rod and the second piston rod back against the pre-tension of the respective pre-tensioned spring element, i.e. it holds the first piston rod back against the pre-tension of the first spring element and the second piston rod back against the pre-tension of the second spring element. The respective spring element can be arranged held in pre-tension between the common holding component and the respective piston, wherein a release of the respective free piston rod end by the common holding component releases the spring element, i.e. it is made possible that its pre-tension is converted into a spring deflection, and thus the respective piston movement can be induced. According to a further preferred embodiment, the common holding component is essentially plate-shaped, i.e. essentially has the shape of a preferably flat plate, which, depending on the use or additional functions, can have recesses and projections or the like, inter alia those of a manufacturing-related nature. As an alternative to this, it is also conceivable that the common holding component can also be designed in the form of a disk, semicircle, or the like, as long as a releasable holding function of the free piston rod ends can be implemented.

According to a further preferred embodiment of the present disclosure, the common holding component has at least one recess for the free end of the first piston rod, thus a so-called first recess, and at least one recess for the free end of the second piston rod, thus a so-called second recess. The free end of the first piston rod, which is arranged opposite to the end of the first piston rod with the first piston fastened thereon, i.e. is arranged remotely from the first container, has a depression in this case, i.e. a so-called first depression, preferably in the form of a groove or the like. Correspondingly, the free end of the second piston rod, which is arranged opposite to the end of the second piston rod having the second piston fastened thereon, i.e. is arranged remotely from the second container, also has a depression, i.e. a so-called second depression, preferably in the form of a groove or the like. Both depressions of the first and the second piston rod are releasably engaged with the common holding component in this case. Correspondingly, at least one section of the respective depression overlaps with a section of the common holding component, wherein this holding component section surrounds the respective recess, so that mechanically pulling the corresponding section of the common holding component out of the respective piston rod depression disengages the connection between the respective free piston rod end and the common holding component and thus releases the respective piston rod for its spring-driven movement as described above.

In order to implement the above-described successive release of the first piston rod and then the second piston rod, a size of the free end of the first and the second piston rod and a size of the respective recess and/or a depth of the respective recess is selected such that the free ends of the first and the second piston rod interact differently with the common holding component. This means that the respective recess-depression combinations are selected so that the combination made up of first recess and first depression are released from one another at a different point in time than the combination made up of second recess and second depression during a movement of the common holding component out of the piston rod end depressions. A chronological sequence of the release of the two free piston rod ends can accordingly be achieved either by selecting the respective size of the respective free piston rod end so that different overlaps are achieved between the respective free piston rod end and the respective recess, or by selecting different depths of the depressions in the piston rod ends, or a combination of these. Overlap or overlap region means here a region in which one of the free piston rod ends is engaged by its depression with the circumferential region of the corresponding recess, at a point in time at which the common holding component holds both piston rod ends in engagement. Correspondingly, an lower side of the free piston rod end at the associated depression overlaps a corresponding part of the circumferential region of the associated recess in the common holding component, so that reference can be made to an engagement region, an overlap region, or also an overlap surface. By pulling the common holding component out of the depressions in the piston rod ends, the corresponding overlap region decreases and the common holding component is continuously disengaged until ultimately no overlap region remains and the corresponding free piston rod end is no longer engaged and is accordingly released from the common holding component. This process occurs in parallel with both free piston rod ends by pulling out the common holding component, wherein a chronological sequence of the release of the two free piston rod ends in succession can be achieved either by selecting different sizes of the free piston rod ends or the corresponding recesses and thus their overlap regions, or by selecting different depths of the depressions in the piston rod ends, whereby their overlap regions are also different, or a combination of these.

With regard to the previously mentioned selected sizes of the free piston rod ends and the respective recess, the first recess in the common holding component for the free end of the first piston rod essentially has a triangular shape and the second recess in the common holding component for the free end of the second piston rod essentially has a semicircular shape, wherein then the free end of the first piston rod also essentially has a triangular shape, and the free end of the second piston rod also essentially has a semicircular shape. As a result, in addition to easier and more error-free assembling of the device during manufacturing, a different overlap between the respective depression and the corresponding recess circumference can also be achieved by way of a clear shape-related assignability of the respective recess to the respective piston rod end. This means in particular that the overlap of the depression in the semicircular shaped piston rod end and the semicircular shaped recess circumference is greater than the overlap of the recess in the triangular shaped piston rod end and the triangular shaped recess circumference, wherein alternative shape combinations having the same effect can also be selected. Additionally or alternatively, the depth of the depression in the free end of the second piston rod can be deeper than the depth of the recess in the free end of the first piston rod, which also results in a chronological sequence of releasing the free end of the first piston rod and then releasing the free end of the second piston rod. Furthermore, due to its semicircular and thus rotatable cross-sectional shape, the free end of the second piston rod can have a projection, for example in the form of a web or a lug, as a rotation lock in order to prevent the free end of the second piston rod from rotating in conjunction with a corresponding depression as a counterpart. In contrast, a corresponding projection at the free end of the first piston rod can be dispensed with, since this is already largely secured against rotation by its triangular shape and the corresponding counterpart.

According to a further preferred embodiment of the present disclosure, the at least one pre-tensioned spring element of the first piston, i.e. the first spring element, moves the first piston together with the first container in relation to the device after the first piston rod is released by the common holding component. Furthermore, the at least one pre-tensioned spring element of the second piston, i.e. the second spring element, after the second piston rod is released, first moves the second piston together with the second container in relation to the device and then moves the second piston in relation to the second container. According to a further preferred embodiment of the present disclosure in this regard, the first substance which is present in the first container is different from the second substance which is present in the second container. Accordingly, mixing the first with the second substance results in a substance mixture which consists of the two substances, as already described in detail at the previous point. Provided that the two containers are brought into fluid connection with each other, the second substance present as a liquid is pushed out of the second container by displacing the second piston toward the corresponding end of the second container and transferred into the first container, in which the liquid mixes the first substance present therein and this can form a corresponding solution. Subsequently, the resulting solution made up of first substance and solution liquid in the first container can be dispensed, by displacing the first piston toward the corresponding container end of the first container, via the injection device, which is in fluid connection with the first container.

The first substance can be a solid, such as a lyophilizate, so that mixing of the solution liquid and lyophilizate results in a reconstitution of the lyophilizate, so that it can then be injected from the device and via the injection device into the patient. In such an application, the first container can also be referred to as a lyophilizate container, and the second container can be referred to as a liquid container. A reconstitution of the lyophilizate is possible in this case, regardless of the orientation of the device relative to gravity. In general, with regard to the piston movements described here, according to a further preferred embodiment of the present disclosure, the first container can have a first container end and a second container end, and the second container can have a corresponding first and second container end, wherein the first and the second piston are axially displaceable between the respective first container end and the respective second container end. Accordingly, by displacing the first piston toward the first container end of the first container, contents of the first container can be dispensed from the first container, and by displacing the second piston toward the first container end of the second container, contents of the second container are dispensed from the second container, wherein in particular if there is a fluid connection between the injection device and the first container, by displacing the first piston toward the first container end of the first container, contents of the first container can be dispensed to the outside via the injection device.

According to a further preferred embodiment of the present disclosure, the conduit device can have a first connection element for a fluid connection with the first container and a second connection element for a fluid connection with the second container, wherein each connection element can be embodied as a needle-like projection for penetrating a septum of the respective container. A septum enables a container to be closed off particularly reliably and tightly. In both cases mentioned, the needle-like projection can be provided in the form of a needle, in particular an obliquely ground hollow cannula. In order to reduce the risk of contamination of the substance to be dispensed, it is advantageous in particular in the case of sterile applications if the penetration means used, such as the needles or hollow cannulas mentioned, are each provided with a flexible protective cap or protective sleeve, which can also be pierced together with the corresponding septum. The use of protective caps or sleeves of this type allows in particular final assembly of the device under non-sterile conditions. Furthermore, the conduit device can have a fluid connection to the injection device, wherein a valve element can be provided in the conduit device, furthermore preferably a one-way valve, thus for example a check valve, for example in the form of a flap valve, which in particular acts as a one-way valve in the fluid connection to the injection device. The valve element can be provided in the conduit device in such a way that a liquid transfer is possible from the second container to the first container, a subsequent liquid transfer from the first container to the second container is prevented, but a liquid transfer from the first container to the injection device is permitted. The connection for the first container and the connection for the injection device can preferably be on the same side of the one-way valve, whereas the connection for the second container is on the other side of the one-way valve. According to a further preferred embodiment of the present disclosure under this aspect, the release of the free end of the first piston rod and the movement thus triggered of the first piston by the first spring element establishes a fluid connection between the conduit device and the first container, for example by piercing or docking the first container by means of the needle-like projection associated with the conduit device for penetrating the septum of the first container. Furthermore, a subsequent release of the free end of the second piston rod and the movement of the second piston thus triggered by the second spring element establishes a fluid connection between the conduit device and the second container, for example also by piercing or docking the second container by means of the needle-like projection associated with the conduit device for penetrating the septum of the second container. Both needle-like projections can be in the form of a needle, which are provided on the conduit device in fluid connection with this and are aligned in the direction of the respective container or the respective first container end, on each of which a septum or the like can be located, in order to enable a fluid connection between needle and container contents. In addition, the second spring element, which preferably has a structurally related greater spring deflection than the first spring element, also has the effect that not only the second container is pressed together with the second piston against the corresponding needle-like projection, but also that after docking of the second container on the needle-like projection and thus one end of the axial movement of the second container, the second piston is moved further by the second spring element and is pressed in the second container against the container end of the second container, whereby the second substance is transferred from the second container via the conduit device into the first container. By way of the time-offset docking of the two containers on the line device achieved in this way, it can be ensured that the liquid is dispensed from the second container into the conduit device only when the first container is already docked.

For the further displacement of the first piston toward the corresponding first container end of the first container in order to transfer the contents of the first container to the injection device and to be dispensed through it, an additional movement device is necessary in the device according to the disclosure, which can be provided, for example, in the form of an additional pre-tensioned spring element which, in addition to the first spring element, is also attached to the first piston and is in operative connection therewith. A subsequent activation of the additional spring element accordingly has the result that when there is a fluid connection between the injection device and the first container, by displacing the first piston toward the first container end of the first container, contents of the first container can be dispensed to the outside via the injection device.

According to a further preferred embodiment of the present disclosure, the device can furthermore have an activation component which is in mechanical operative connection with the common holding component. This means that the activation component and the common holding component can interact mechanically with one another, wherein a movement of the activation component in particular results in the previously described movement of the common holding component in its longitudinal direction. Correspondingly, the movement of the common holding component in its longitudinal direction, which triggers the successive release of the first piston rod and the second piston rod, can be induced by a movement of the activation component. It is a further preferred embodiment of the present disclosure that a longitudinal axis of the activation component is arranged essentially perpendicular to the longitudinal axis of the common holding component, i.e. essentially in parallel to the longitudinal axes of the two piston rods and thus the two containers, wherein a movement direction of the activation component in its longitudinal direction preferably extends essentially perpendicular or essentially at right angles to the movement direction of the common holding component in its longitudinal direction. Preferably, the activation component can have a cascade surface and the common holding component can have an activation recess, wherein the activation component having the cascade surface is arranged in the activation recess, and pulling the activation component out of the activation recess induces an axial movement of the common holding component. For example, the pulling out of the activation component can be achieved here by a removal of a cover of the device according to the disclosure, in particular the activation element can be connected to the cover and thus can be removed by way of unpacking and activating the device during the unpacking of the device, whereby a further separate step and a further separate action by the user are not required to reconstitute the lyophilizate in the device. Alternatively thereto, the above-described activation by moving the common holding component in its longitudinal direction in order to trigger the successive release of the first piston rod and the second piston rod can be achieved by an alternative operating mechanism, which for example consists of a pin-shaped actuating element connected to the common holding component and a corresponding control groove in the cover, as can be seen in more detail below in the description of the figures.

According to a further aspect of the present disclosure, moreover a method for dispensing at least one substance, in particular to a patient, is provided, wherein a device as described above is used for the method according to the disclosure. Correspondingly, the present method according to the disclosure can be an autoinjection by the above-described device, and the features and sequences already described above for the device can accordingly also be used for the method according to the disclosure.

The method according to the disclosure comprises, in particular, a step of moving the activation component, which is in operative connection with the common holding component, along its longitudinal axis, whereby the common holding component moves essentially in its longitudinal direction, in particular perpendicular to the movement direction of the activation component, and first releases the engagement between the common holding component and the free end of the first piston rod and subsequently releases the engagement between the common holding component and the free end of the second piston rod. Correspondingly, the movement of the common holding component in its longitudinal direction, which triggers the successive release of the first piston rod and the second piston rod, can be induced by a movement of the activation component in its longitudinal direction or along its longitudinal axis. The release of the free end of the first piston rod due to the corresponding first spring element can establish a fluid connection between the conduit device and the first container, and the subsequent release of the free end of the second piston rod due to the corresponding second spring element can establish a fluid connection between the conduit device and the second container, wherein moreover the contents of the second container are then transferred via the conduit device into the first container due to the spring deflection of the second spring element. Further, the method may include an additional step of displacing the first piston toward the first end of the container of the first container, whereby the contents of the first container are dispensed via the injection device. This has the advantage that after the contents of the two containers have been mixed by a single action by the user, namely by moving the activation component, and after the device has been attached to the body of the user, only a second actuating action of the user is necessary in the sense of the additional step for triggering the injection. In particular, the injection triggering step can consist of pressing a button. As a result, mechanical forces can be transmitted to components of the device in a predefined time sequence. The present disclosure thus manages with a minimum of actions on the part of the user. The operation of the device becomes simpler, more pleasant, and less prone to errors. Details of the respective processes have already been described in conjunction with the preceding description of the device according to the disclosure and are therefore not repeated at this point.

As possibly used here and in the appended claims, the singular forms "a"/"an"/"one" and "the"/"the"/"the" may also include their plural forms, unless the context clearly indicates otherwise. Similarly, the words "comprise", "contain", and "have" are to be understood both as "exclusively" and "not exclusively", that is to say in the sense of "including but not limited to . . . " The terms "several", "multiple", or "plurality" usually refer to two or more, i.e. 2 or >2, including further integer multiples of 1, wherein the terms "individually" or "alone" refer to one (1), thus "=1". Furthermore, the expression "at least a" or "at least one" is to be understood as one or more, i.e. 1 or >1, likewise with integral multiples. When the word "between" is used to describe a numerical range, the boundary points of the named range are explicitly intended to be considered part of the range. In addition, the words "herein," "above," "before", and "below" or "hereinafter" and words with similar meanings when used in this specification are intended to refer to this specification as a whole, and not to specific parts of the specification.

The following discussion of specific embodiments in this specification is not intended to be exhaustive, or the disclosure herein is not intended to be restricted to the precise form disclosed. While specific embodiments and examples of the disclosure described herein are illustrative, various equivalent modifications are possible within the scope of the disclosure as would be apparent to one skilled in the art in the present technical field. Specific technical elements of the described embodiments can be combined with or replaced by technical elements in other embodiments. In the drawings, the same reference signs denote the same elements in order to avoid repetition, and parts which a person skilled in the art can implement without specific knowledge can be omitted for the sake of clarity. While advantages associated with certain embodiments of the disclosure are described in conjunction with these embodiments, other embodiments may also have these advantages without explicitly citing the same.

The following examples are intended to illustrate specific embodiments of the present disclosure with reference to the figures. All specific modifications, as they are also discussed below, are not to be construed as such as restrictions to the scope of the present disclosure. It will be apparent to those skilled in the art that various alterations, changes, and modifications can be made without departing from the scope of the present disclosure as defined by the appended claims. Further aspects and advantages of the present invention result from the following description of the preferred embodiments illustrated in the figures.

DETAILED DESCRIPTION

In the following description of the preferred embodiments of the disclosure, the figures represent the subject of the invention only schematically. Exemplary embodiments of the disclosure are illustrated in the set of drawings and will be described in greater detail below.

Figure 1:
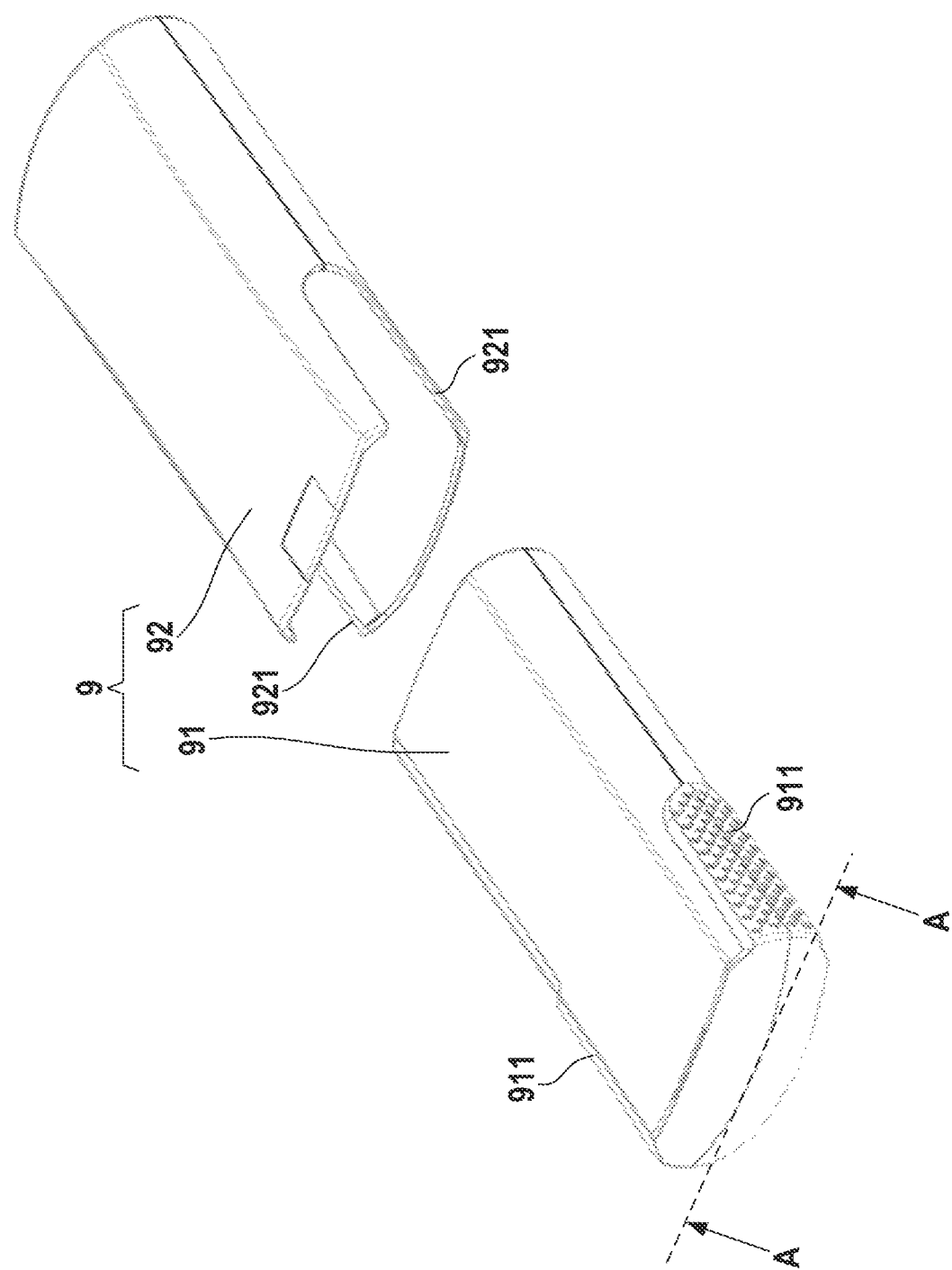
FIG. 1 shows a perspective schematic view of an device according to the disclosure according to one preferred embodiment in an exploded view.

FIG. 1 shows a perspective schematic view of a device 9 according to the disclosure according to one preferred embodiment of the disclosure in an exploded view. The device 9 is shown in two disassembled main components, namely a main body 91 of the device 9 and a cover 92 which at least partially covers the main body 91 in the assembled state of the device 9. In the preferred embodiment shown here, the main body 91 has an essentially rectangular shape having rounded edges. The cover 92 has a hollow shape corresponding to the shape of the main body 91 to be inserted, having one open side, wherein recesses 921 are provided on both sides on the open side of the cover. Gripping strips 911 provided at a corresponding point on the main body 91 are inserted into these recesses 921 in the assembled state in order to make it easier for a user to pull the main body 91 out of the cover 92 or to remove the cover 92 from the main body 91.

Figure 2:
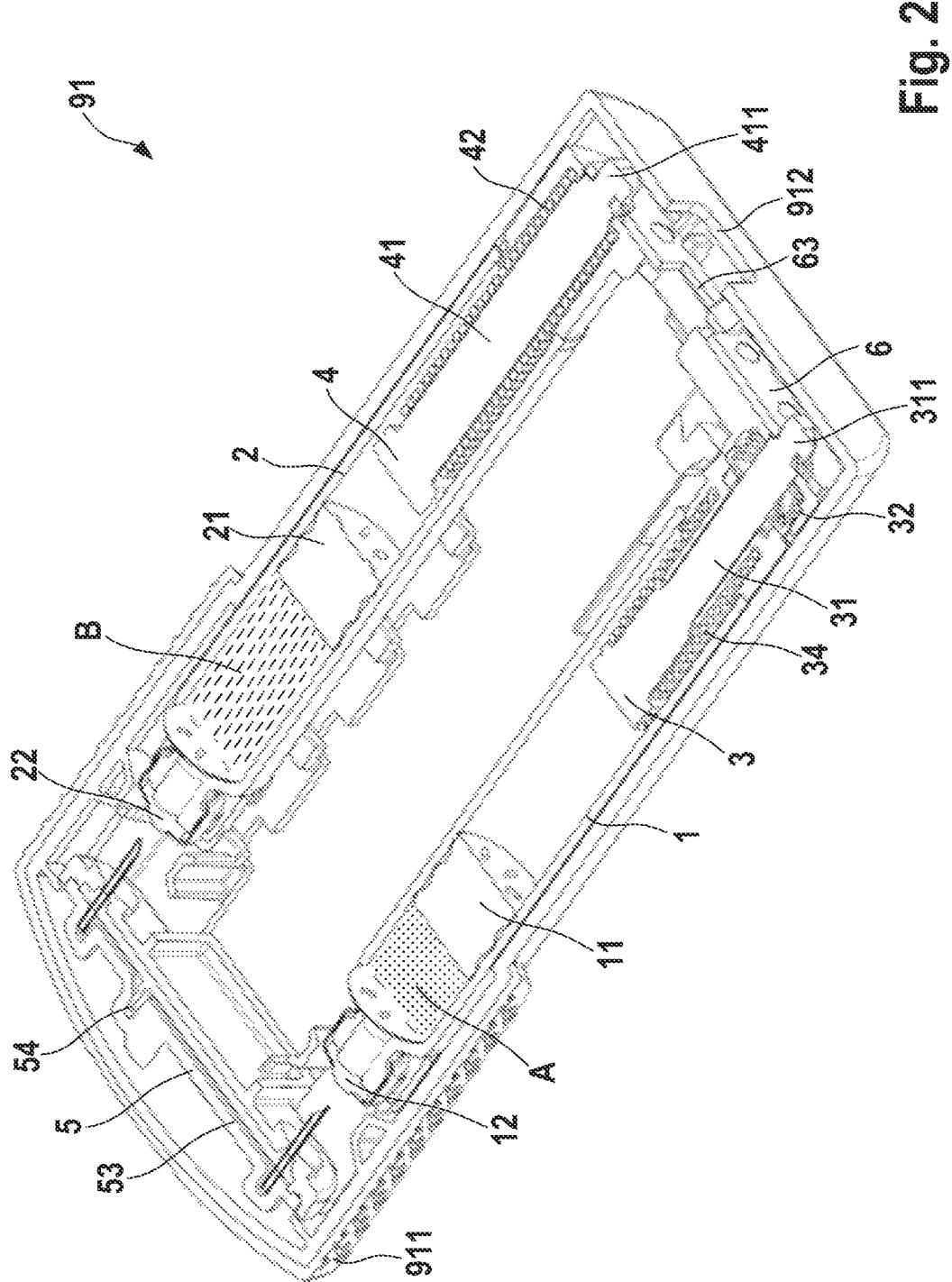
FIG. 2 shows a perspective schematic view of a main body of the device shown in FIG. 1 in an illustration in longitudinal section.

The main body 91 shown in FIG. 1 is shown in FIG. 2 in an illustration in section along line A-A along its longitudinal axis. It can be seen that the main body 91 has an opening 912 at one end thereof, which is intended to be inserted into the cover 92 in the assembled state. In addition, a further opening (not shown) covered by a seal is provided on the main body 91, for example on the lower side of the main body 91, the function of which will be explained later. In the otherwise essentially closed main body 91 there is, inter alia, a first container 1 in which a first substance A is accommodated in a closed manner by a stopper 11, wherein the substance A in the present embodiment is in the form of a lyophilizate. The other end of the first container 1, i.e. the end of the first container 1 opposite to the stopper 11, which can also be referred to as the first end of the first container 1, is closed by a septum 12, for example. The first container 1, which in this sense can also be referred to as a lyophilizate container 1, is arranged in the present case on the left side in FIG. 2. Furthermore, there is a second container 2 in the main body 91, in which a second substance B is accommodated in a closed manner by a stopper 21, wherein the substance B in the present embodiment is in the form of a solution liquid for reconstitution of the lyophilizate. The other end of the second container 2, i.e. the end of the second container 2 opposite to the stopper 21, which can also be referred to as the first end of the second container 2, is closed by a septum 22, for example. The second container 2, which in this sense can also be referred to as the solution liquid container 2, is arranged in the present case on the right side in FIG. 2. Both containers 1 and 2 are interchangeably arranged in the main body 91.

Figure 3:
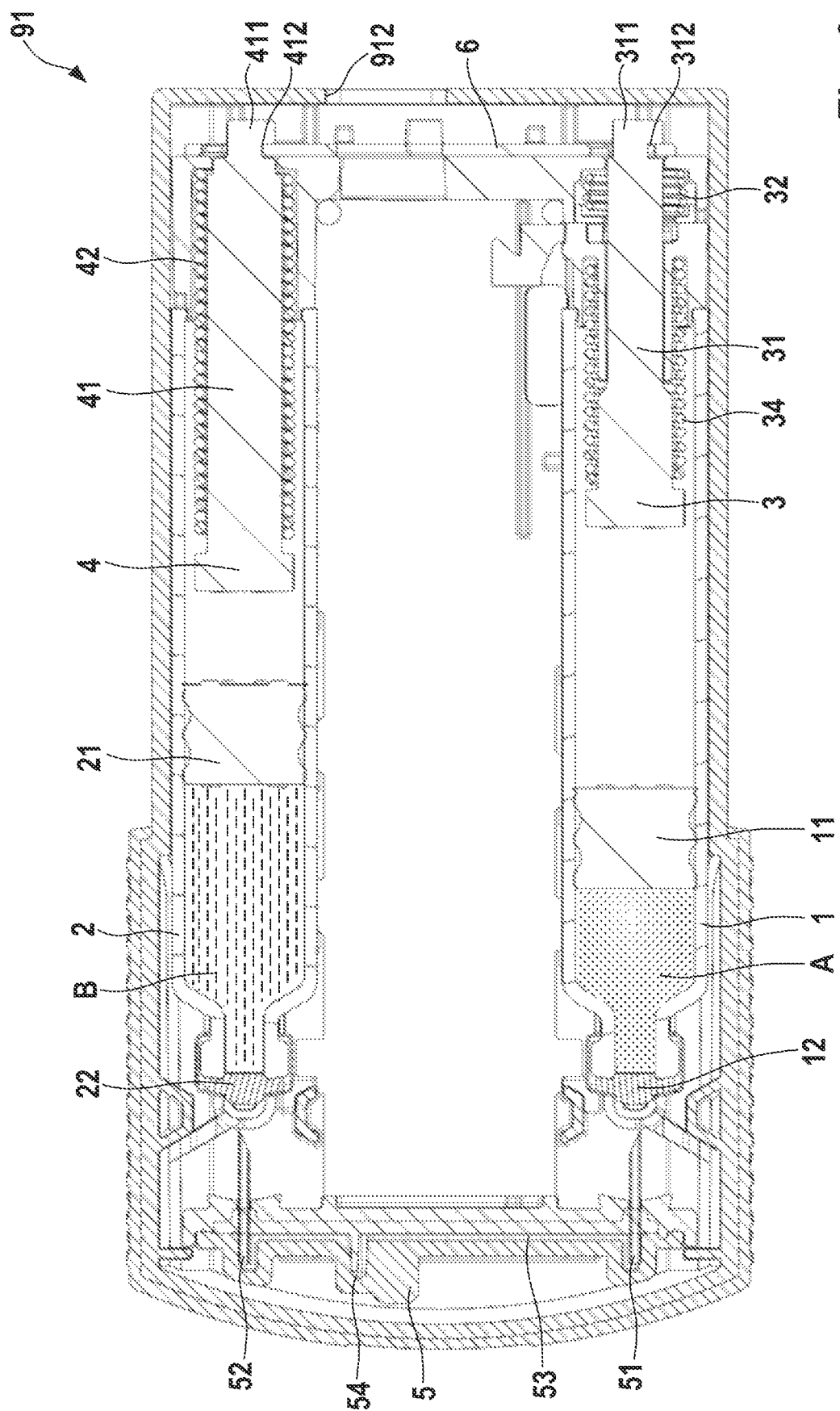
FIG. 3 shows a top view of the view shown in FIG. 2.

As can furthermore be seen both in FIG. 2 and also in the top view in FIG. 3 corresponding thereto, moreover a first piston 3 having a first piston rod 31 is arranged in the main body 91, wherein the first piston or its piston roof is guided essentially within the container 1 so that the piston roof can come into contact with the opposing side of the stopper 11, so that the stopper 11 can be pressed against the septum-bearing end of the first container 1, which represents a first end of the first container 1. Furthermore, a second piston 4 having a so-called second piston rod 41 is arranged in the main body 91, wherein the second piston 4 or its piston roof is guided essentially within the second container 2 in such a way that the piston roof can come into contact with the opposing side of the stopper 21, so that the stopper 21 can be pressed against the septum-bearing end of the second container 2, which represents a first end of the second container 2. Both containers 1 and 2 are installed in the main body 91 in such a way that they are movably mounted or guided in the main body 91 in their longitudinal direction, as is indicated in FIGS. 2 and 3. When the containers 1 and 2 move in the direction of their septum-bearing ends, the respective septum 12, 22 is pressed onto a respective fixed needle 51, 52, whereby the septa 12, 22 are pierced by the needles 51, 52. This piercing of the septa 12, 22, and thus the piercing of the container 1, 2 establishes a fluid connection between the contents of the container 1, 2 and a conduit channel 53 of a conduit device 5, which is arranged fixed on the inner side of the main body 91 at a left end shown in FIGS. 2 and 3. The conduit device 5, which can consist of several wall components due to the manufacturing process, as indicated in FIGS. 2 and 3, not only holds the needle 51 and the needle 52 in place, aligned with the respective septum 12, 22, but also forms the conduit channel 53 in its interior. A one-way valve 54 is also provided in the conduit channel 53, here in the form of a rubber lip which, like a flap, rests on one side against an inner wall of the line channel 53 and thus allows fluid to flow from the second container 2 into the first container 1 in the present embodiment, but prevents a backflow of a fluid from the first container 1 into the second container 2. In addition to the components already described, a preferably sealed opening (not shown) for connecting an injection device (not shown) is also provided in the conduit channel 53, namely in the area of the conduit channel 53 which, starting from the one-way valve 54, lies on the side of the first container 1. The injection device (not shown) can be designed such that it can also pierce the sealed opening by way of a needle or the like, or that the injection device is already connected to the sealed opening. The injection device is used to dispense a substance located in the conduit channel 53 and/or in the container 1 to a user by injection, preferably autoinjection. In addition, the previously mentioned opening (not shown) covered by a seal is used, which is provided for example on the lower side of the main body 91 and through which the injection device can eject the substance to be dispensed by piercing.

Figure 4:
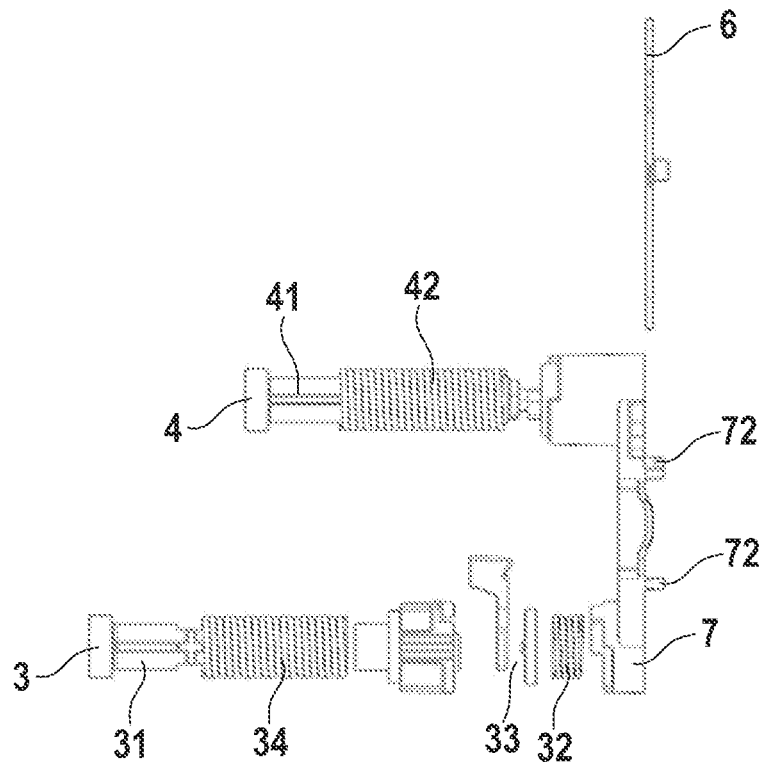
FIG. 4 shows a top view of a part of the view shown in FIG. 2 in an exploded view, which in particular shows an interaction between the common holding component and the two piston rods.
Figure 5:
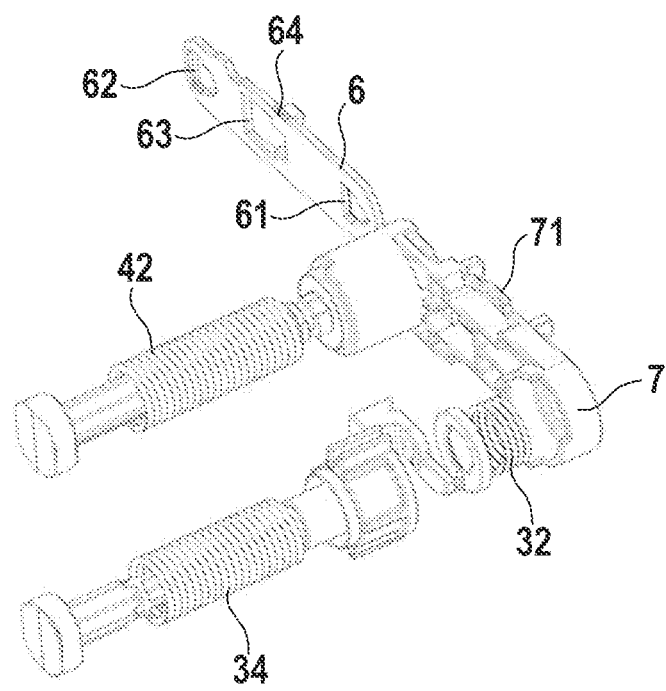
FIG. 5 shows a perspective view of the illustration shown in FIG. 4.

The above-described piercing of the container 1, 2 by piercing the septa 12, 22 by means of the needle 51, 52 is effectuated, as discussed, by moving the containers 1, 2 in their axial direction. In order to induce such a movement of the first container 1, the first container 1 is provided in the preferred embodiment shown with a first pre-tensioned spring element 32, here in the form of a spiral spring 32, which is held at an end facing away from the first container 1 by bearing against a guide component 7 and is in operative connection with the first container 1 at an end facing toward the first container 1 via an intermediate component 33, so that a deflection of the pre-tensioned spiral spring 32 causes a longitudinal displacement of the first container 1 in the direction toward the needle 51, in order to pierce the septum 12 of the first container 1 using the needle 51. The spiral spring 32 is pre-tensioned by clamping between the intermediate component 33 and the guide component 7, wherein the spiral spring 32 is arranged around the first piston rod 31 and a free end 311 of the first piston rod 31 of the first piston 3 is held in place by a holding component 6. The holding component 6 is also referred to as a common holding component 6 because it not only holds in place the free end 311 of the first piston rod 31 of the first piston 3, but also the free end 411 of the second piston rod 41 of the second piston 4 by engaging with them. Moreover a further pre-tensioned spring element 34 in the form of a spiral spring 34 is arranged on the piston construction of the first piston 3 of the first container 1 in the present embodiment described, which can be released after triggering, for example by a separate mechanism to be actuated by the user, so that a deflection of the further pre-tensioned spiral spring 34 is effectuated, which effectuates a movement of the first piston 3, guided via the first piston rod 31, in the direction toward the fluid connection between the first container 1 and the conduit channel 53 already established by the first pre-tensioned spring element 32, so that contents of the first container 1 can be pressed in the conduit channel 53 and additionally through the injection device (not shown) and out of the main body 91 of the device 9. A more precise structure of the interaction of piston 3, piston rod 31, first pre-tensioned spring element 32, intermediate component 33, and further pre-tensioned spring element 34 can also be seen in FIGS. 4 and 5, in which the general interaction between the two piston structures of pistons 3 and 4 and their spring elements 32, 34, and 42 as well as the common holding component 6, cut away from the remaining components of the device 9, are shown in an exploded view in perspective and in a top view for simplified representation.

Accordingly, in order to induce a piercing movement of the second container 2, the second container 2 in the preferred embodiment shown is provided with a second pre-tensioned spring element 42, here in the form of a spiral spring 42, which is held at an end facing away from the second container 2 by contact with the guide component 7 and is in operative connection at an end facing toward the second container 2 by way of the second piston 4 with the second container 2, so that a deflection of the pre-tensioned spiral spring 42 effectuates a longitudinal displacement of the second piston 4 toward the stopper 21 and thereby a longitudinal displacement of the second container 2 in the direction toward the needle 52, in order to pierce the septum 22 of the second container 2 using the needle 52. The spiral spring 42, which is arranged around the second piston rod 41, is pre-tensioned by clamping between the inner side of the piston 4 and the guide component 7, wherein a free end 411 of the second piston rod 41 of the second piston 4 is held in place by the common holding component 6, which also holds the free end 311 of the first piston rod 31 of the first piston 3. Correspondingly, releasing the pre-tensioned spiral spring 42 has the result that the second piston 4 is moved and strikes the stopper 21, is moved together with this stopper due to the dynamic pressure of the incompressible liquid arranged in the container 2 axially toward the needle 52 and thus establishes the fluid connection between conduit channel 53 and contents of the container 2, which provides an outlet for the dynamic pressure in the container 2. The spiral spring 42 then presses the piston 4 together with the stopper 21 further and thus causes the contents of the second container 2 to be conveyed into the conduit channel 53, past the one-way valve 54 and further into the first container 1. Correspondingly, in the present embodiment, the incompressible solution liquid, which is present as contents in the second container 2, i.e. in the solution liquid container 2, is pressed into the first container 1, i.e. the lyophilizate container 1, in which the solution liquid is mixed with the lyophilizate and thus induces a reconstitution of the lyophilizate. The resulting solution can then be conveyed out of the first container 1 as a substance to be dispensed (injected) by triggering the further spiral spring 34 and dispensed to the outside through the injection device (not shown), preferably by autoinjection to the user himself. It can already be seen from the illustrations in FIGS. 2 to 5 that the pre-tensioned spiral spring 32 for piercing the first container 1 is dimensioned significantly smaller than the two spiral springs 34 and 42, whereby a resulting deflection or elongation of the spiral spring 32 is significantly shorter than in the other two spiral springs 34 and 42. This is due to the fact that only a slight axial displacement of the container 1 is necessary for the exclusive piercing of the first container 1 by the spiral spring 32.

Figure 6A:
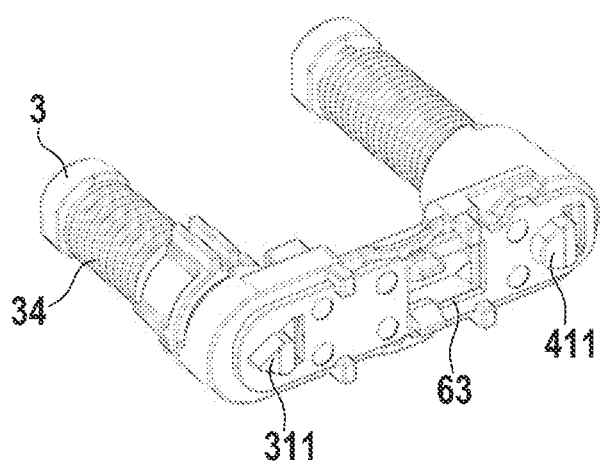
FIG. 6A shows a releasing process of the two piston rod ends by way of a movement of the common holding component in three exemplary steps.
Figure 6B:
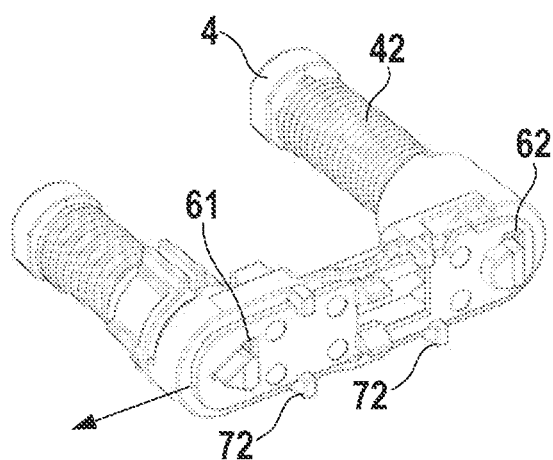
FIG. 6B shows a releasing process of the two piston rod ends by way of a movement of the common holding component in three exemplary steps.
Figure 6C:
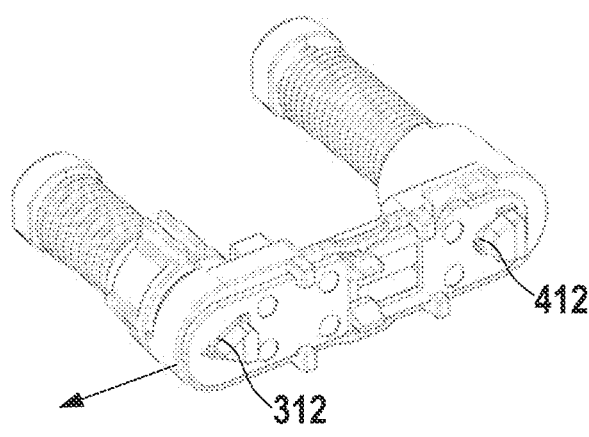
FIG. 6C shows a releasing process of the two piston rod ends by way of a movement of the common holding component in three exemplary steps.

In FIGS. 6A to 6C, a process of the time-offset release of first the first pre-tensioned spiral spring 32 and then the second pre-tensioned spiral spring 42 is shown. A starting state is shown in FIG. 6A, as can also be seen in FIGS. 2 and 3. In this starting state, the common holding component 6 holds the two free ends 311, 411 of the two piston rods 31, 41 in engagement, so that the two spiral springs 32, 42 are held in their pre-tensioned state, and no movement of the pistons 3, 4 or the containers 1, 2 takes place. As can be seen, inter alia, from FIG. 6A, the free end 311 of the first piston rod 31 has a triangular shape. A recess 61, which corresponds to the free end 311 of the first piston rod 31 and which is provided in the common holding component 6 for holding the free end 311 of the first piston rod 31, also has a triangular shape. Here, however, the triangular shape of the recess 61 is larger than the triangular shape of the free end 311 of the first piston rod 31, as can be seen in each of FIGS. 6A to 6C. In the free end 311 of the first piston rod 31, a depression in the form of a groove 312 is also provided, see also FIG. 3, into which a peripheral region of the triangular recess 61 is inserted in the starting state shown in FIG. 6A. Similarly, the free end 411 of the second piston rod 41 has a semicircular shape. A recess 62, which corresponds to the free end 411 of the second piston rod 41 and which is provided in the common holding component 6 for holding the free end 411 of the second piston rod 41, also has a semicircular shape. Here, however, the semicircular shape of the recess 62 is again larger than the semicircular shape of the free end 411 of the second piston rod 41, as can be seen in each of FIGS. 6A to 6C. A depression in the form of a groove 412 is also provided in the free end 411 of the second piston rod 41, see also FIG. 3, into which a peripheral region of the semicircular recess 62 is inserted in the starting state shown in FIG. 6A. The size difference between the recesses 61, 62 and the respective free ends 311, 411 is due to the fact that the free ends 311, 411 should pass freely through the corresponding recess 61, 62 without tilting after a respective release, i.e. in order to ensure the release process of the free ends 311, 411.

In the present embodiment, the relationship between the triangular shape of the free end 311 of the first piston rod 31 and the triangular shape of the recess 61 is selected so that the overlap region in the starting state is smaller than an overlap region between the semicircular shape of the free end 411 of the second piston rod 41 and the semicircular shape of the recess 62. In order to cause the two free ends 311, 411 of the two piston rods 31, 41 to release, the common holding component 6 can be moved in its longitudinal direction, and thus essentially perpendicular to the longitudinal directions of the two piston rods 31, 41 so that the common holding component 6 is pulled out of the grooves 312, 412. This pulling-out process occurs in both free piston rod ends 311, 411 in parallel to one another by pulling out the common holding component 6. Due to the fact that in the first piston rod 31, the overlap region between the groove 312 and the surroundings of the recess 61 is smaller than the overlap region between the groove 412 and the surroundings of the recess 62 in the second piston rod 41, the step-by-step pulling out of the common holding component 6 first results in release of the free end 311 of the first piston rod 31, see also FIG. 6B, and thus piercing of the first container 1. Only then does the further pulling out of the common holding component 6, as shown in FIG. 6C, result in loosening of the free end 411 of the second piston rod 41, and thus piercing of the second container 2 and then pushing the contents of the second container 2 through the conduit channel 53 past the one-way valve 54 into the fluid-connected container 1, which results in the reconstitution of the lyophilizate. The contents of the container 1 increase accordingly by the volume pressed in, so that the stopper 11 of the first container 1 is pressed backwards in the direction of the first piston 3. For this purpose, in the starting state, as shown in FIGS. 2 and 3, sufficient space is left between the stopper 11 and the piston 3 so that the stopper 11 has room to move backwards. For this purpose, it is obviously necessary to allow the air displaced back to escape past the piston 3, as shown, inter alia, in FIG. 3.

Figure 7:
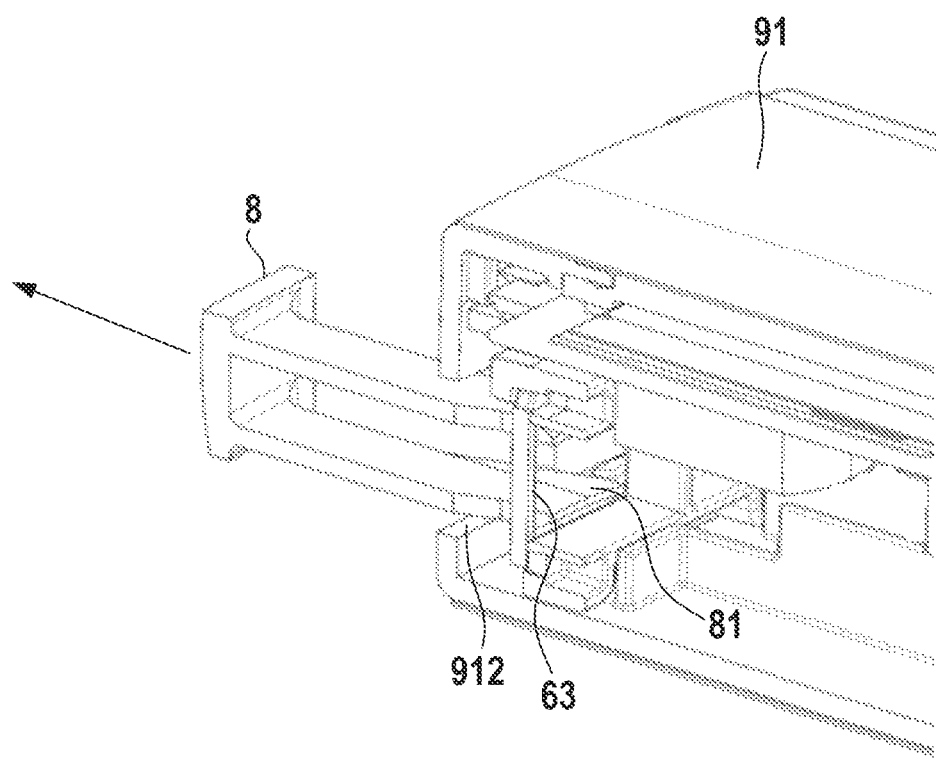
FIG. 7 shows an activation of the common holding component of the device of the preferred embodiment shown in the previous figures by an activation component.

On closer inspection of the illustrations in FIGS. 6A to 6C, an arrangement of three detent depressions 64 can also be recognized on an upper side of the common holding component 6, which can be hooked in preferably three different positions by a detent lug 71 attached in one piece to the guide component 7. Correspondingly, the combination of detent depressions 64 and detent lug 71 is used to guide the movement of the common holding component 6 step-by-step by locking when the device 9 is used in a principally horizontal direction from a starting position as shown in FIG. 6A to an intermediate position for releasing the first piston rod 31 as shown in FIG. 6B to an end position to release the second piston rod 41, i.e. in the three positions mentioned. The general movement of the common holding component 6 is, as shown here, guided by guide rails 72 which are attached to the guide component 7. As finally shown in FIG. 7, the device 9, in particular in the present preferred embodiment an inner side of the cover 92, has an activation component 8 possibly connected to it, which in the assembled state of the device 9 passes through the opening 912 in the main body 91 and through a recess 63 or an activation recess 63 in the common holding component 6. The guide component 7 also has a recess (not shown) corresponding to the activation recess 63 in order to enable the activation component 8 to pass through the opening 912, the activation recess 63, and the guide component recess (not shown). The activation component 8, which is preferably formed by two longitudinal webs, has a projection 81 in the form of a cascade surface on each web front side so that pulling out the activation component 8 in its axial direction triggers pressing of the common holding component 6 in the axial direction of the common holding component 6, which is essentially perpendicular to the axial direction of the activation component 8, whereby the common holding component 6 is moved to release the two free ends 311, 411 of the two piston rods 31, 41. Correspondingly, in the present preferred embodiment, a longitudinal axis of the activation component 8 is arranged essentially perpendicular to the longitudinal axis of the common holding component 6, i.e. essentially in parallel to the longitudinal axes of the two piston rods 31, 41 and thus the two containers 1, 2, wherein a pulling-out direction of the activation component 8 in its longitudinal direction preferably extends essentially perpendicular or essentially at right angles to the movement direction of the common holding component 6 in its longitudinal direction. Due to the combination of the cascade surface and the activation recess, the activation component 8 and the common holding component 6 are accordingly in a mechanical operative connection, so that the movement of one component, for example the activation component 8, causes a movement of the other component, in this case the common holding component 6.

Figure 8A:
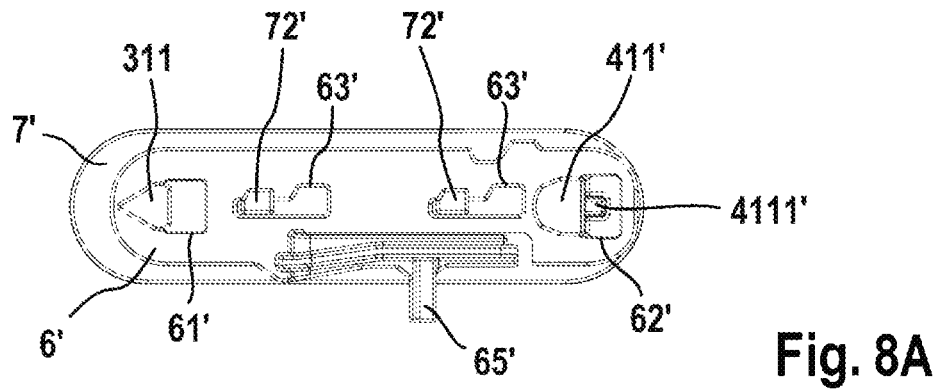
FIG. 8A shows a releasing process of the two ends of the piston rod by way of a movement of an alternative embodiment of the common holding component in three exemplary steps, triggered by an alternative mechanism of action.
Figure 8B:
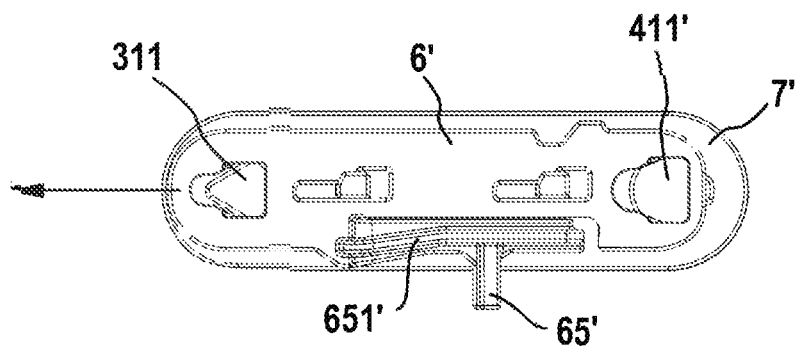
FIG. 8B shows a releasing process of the two ends of the piston rod by way of a movement of an alternative embodiment of the common holding component in three exemplary steps, triggered by an alternative mechanism of action.
Figure 8C:
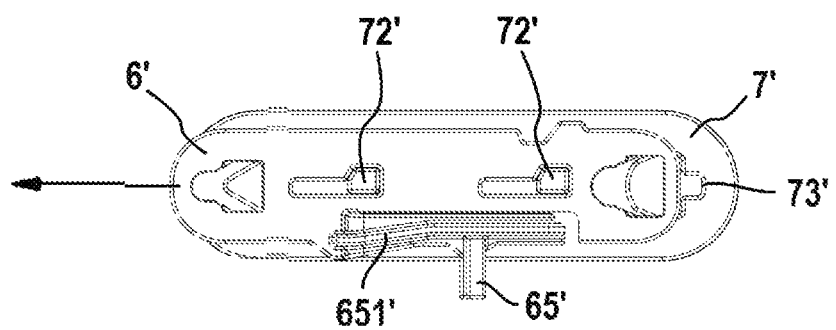
FIG. 8C shows a releasing process of the two ends of the piston rod by way of a movement of an alternative embodiment of the common holding component in three exemplary steps, triggered by an alternative mechanism of action.

FIGS. 8A to 8C show an alternative embodiment of a combination made up of guide component 7' and common holding component 6', wherein FIGS. 8A to 8C show, similarly to that shown in FIGS. 6A to 6C, a process of the time-offset release of firstly the first pre-tensioned spiral spring 32 and then the second pre-tensioned spiral spring 42. The basic sequence of the release process remains essentially unchanged in comparison to the previously described embodiment, wherein only the actuation of the common holding component 6' and the guiding of the common holding component 6' on the guide component 7' take place in a different manner, as will described in more detail below.

With regard to the alternative guiding of the common holding component 6' on the guide component 7', in the embodiment described here, the common holding component 6' is guided here by two guide rails 72' arranged on the inside, which each extend in a recess 63' farther inward, for example in the form of a continuous guide groove, instead of the guide rails 72 arranged on the outside for this purpose. The guide rails 72' each essentially have the shape of an upside-down letter L (=⌐) and each extend from an outwardly oriented surface of the guide component 7' in the direction of the common holding component 6' and through it, more precisely through the respective recess 63'. Each recess 63' shows at a first end, shown in the figures on the right side, a so-called feedthrough expansion for free passage of the respective guide rail 72', as well as a correspondingly narrowed guide groove adjoining the feedthrough extension, which accommodates the axially extending, longer section of the respective L-shaped guide rail 72' and guides it.

With regard to the alternative actuation of the common holding component 6', FIG. 8A shows a starting state before the release process, in which the common holding component 6' holds the free end 311 of the first piston rod 31 and an alternative embodiment of a free end 411' of the second piston struts 41 engaged, so that the two spiral springs 32, 42 are held in their pre-tensioned states and, accordingly, neither the pistons 3, 4 nor the containers 1, 2 can move. The above-mentioned alternative embodiment of the free end 411' of the second piston rod 41 differs from the previously described embodiment of the free end 411 of the second piston rod 41 in particular in that it additionally has an outwardly protruding projection 4111' in the form of a web or the like, which is arranged opposite to the round portion of the substantially semicircular shape of the free end 411' of the second piston rod 41. The projection 4111', also referred to as an anti-rotation lock or anti-rotation lock projection, extends in a corresponding groove 73', which is provided in the guide component 7' and is adapted to the shape of the projection 4111', and is used to prevent the free end 411' of the second piston rod 41, and thus the entire second piston rod 41, from rotating, wherein such a rotation can occur, for example during assembly of the device according to the disclosure or also in the event of a shock-related vibration during the transport of the device according to the disclosure.

As can be seen, inter alia, from FIG. 8A, the free end 311 of the first piston rod 31, similar to the embodiment described above, also has a triangular shape which, taken in and of itself, offers a rotation lock due to its shape. A recess 61', which corresponds to the free end 311 of the first piston rod 31 and is provided in the common holding component 6' for holding the free end 311 of the first piston rod 31, has a substantially corresponding, triangular-looking shape in which a front tip is rounded to correspond to, for example, the semicircular shape of the groove 312. In the present alternative embodiment, the relationship between the triangular shape of the free end 311 of the first piston rod 31 and the essentially triangular shape of the recess 61' is selected similarly to the previously described embodiment, so that its overlap region in the starting state is smaller than an overlap region between the semicircular shape of the free end 411' of the second piston rod 41 and the semicircular shape of the recess 62'. In order to effectuate a release of the two free ends 311, 411' of the two piston rods 31, 41, the common holding component 6' can be moved in its longitudinal direction, and thus essentially perpendicular to the longitudinal directions of the two piston rods 31, 41, so that the common holding component 6' is pulled out of the grooves 312, 412. This pulling out of the common holding component 6' from the grooves 312, 412 is also referred to as a release process. The release process takes place at both free piston rod ends 311, 411' by pulling the common holding component 6' shown in FIGS. 8A to 8C to the left in the plane of the figure, see also the arrows shown in FIGS. 8B and 8C. Due to the fact that in the first piston rod 31 the overlap region between the groove 312 and the surroundings of the recess 61' is smaller than the overlap region between the groove 412 and the surroundings of the recess 62' in the alternative free end 411' of the second of the second piston rod 41 similarly as in the previously described embodiment, the illustrated step-by-step pulling out of the common holding component 6' first results in loosening/release of the free end 311 of the first piston rod 31, as shown in FIG. 8B, and thus piercing of the first container 1. Only then does the further movement of the common holding component 6' as shown in FIG. 8C result in loosening/release of the free end 411' of the second piston rod 41, and thus piercing of the second container 2 as well as subsequent pressing of the contents of the second container 2 through the conduit channel 53 past the one-way valve 54 into the fluid-connected container 1, which results in the reconstitution of the lyophilizate.

Figure 9A:
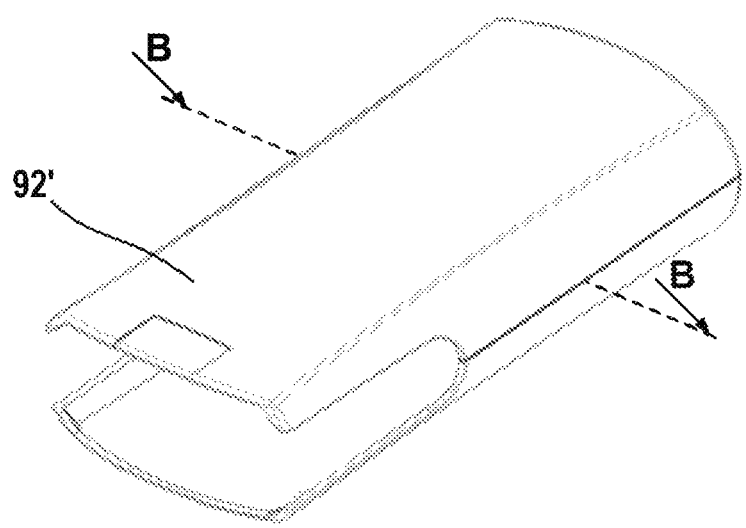
FIG. 9A shows a perspective schematic view of an alternative embodiment of a cover of the device according to the disclosure.
Figure 9B:
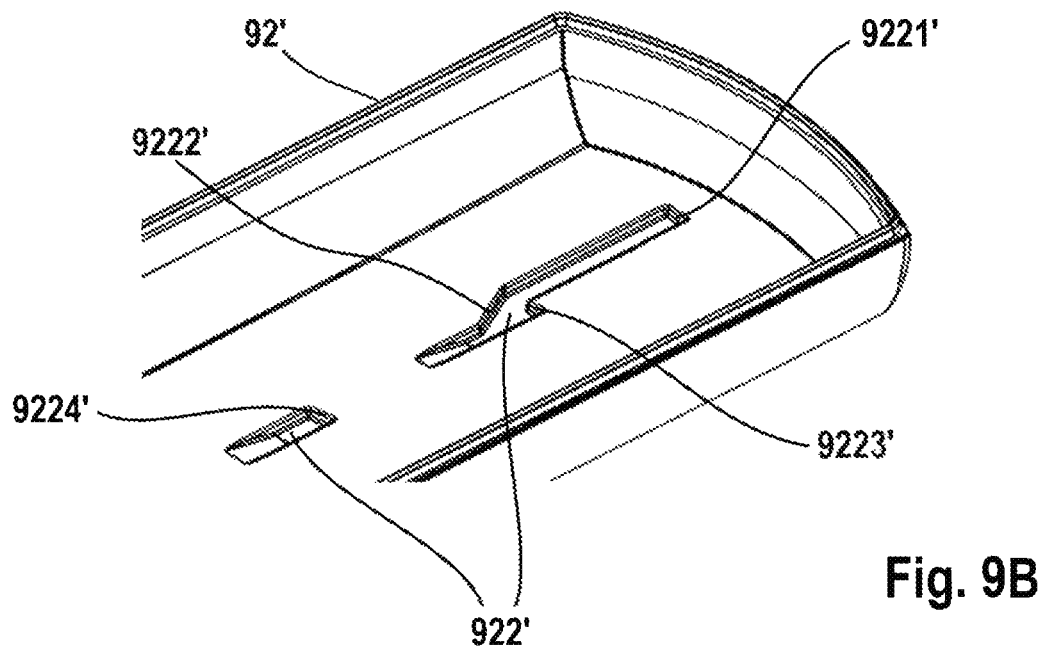
FIG. 9B, shows a perspective schematic view of an inner side of a lower half of the cover shown in FIG. 9A, shown in a top view of a sectional plane extending along section line B-B.

On closer inspection of the illustrations in FIGS. 8A to 8C, an actuating element 65' in the form of an outwardly protruding pin or bolt can be seen on an lower side of the common holding component 6', which is connected to the common holding component 6' via a spring mechanism 651'. By actuating/moving the pin-shaped actuating element 65 ', the desired movement of the common holding component 6' and thus the previously described release process of the two free ends 311, 411 'of the piston rods 31, 41 are effectuated. In order to actuate the actuating element 65' accordingly, a so-called guide or control groove 922', which is formed in two parts in the present described embodiment, for example, is provided on an inner side of an alternative embodiment of a cover 92', as shown in FIGS. 9A and 9B. In an assembled state of the device 9, the actuating element 65' is accordingly arranged inside a first section of the control groove 922'. In a starting state, as shown in FIG. 8A, the actuating element 65' is correspondingly located at a first end 9221' of the longer, first section of the control groove 922', as shown in FIG. 9B on a right side of the inner side of the lower half the alternative cover 92'. When the cover 92' is removed from the main body 91 of the device 9, a corresponding movement of the actuating element 65' extends away from the first end 9221' towards an inclined surface or incline 9222' of the control groove 922' arranged downstream. By moving the actuating element 65' along this incline 9222', which is caused by further pulling of the cover 92' off of the main body 91, the movement of the holding component 6', which is integrally connected to the actuating element 65', takes place, as shown in FIGS. 8A to 8C. After the actuating element 65' has been moved completely along the entire incline 9222', the state shown in FIG. 8C is finally reached in which both free ends 311, 411' of the piston rods 31, 41 are released from the holding component 6'.

From a certain state of the release movement, more precisely from the release of the free end 311 of the first piston rod 31 of the first piston 3, the common holding component 6' must no longer be able to move back into its original starting position, in order to prevent a user from getting the impression of a unused device 9, although essential reconstitution processes have already taken place. In order to prevent the actuating element 65 'and thus the common holding component 6' from being moved back by accidental or intentional pushing back of the cover 92', the control groove 922' has a first stop 9223' on a side opposite to the incline 9222', on which the actuating element 65 'comes into contact in the event of the cover 92' being pushed back and thus prevents the actuating element 65' from moving back further.

When the progress of pulling the cover 92' off the main body 91 is desired, the actuating element 65' leaves the first section of the control groove 922' after the incline 9222' and, for example, supported by a ramp or the like, and then optionally enters a shorter, second section the control groove 922', as shown on the left in FIG. 9B. This shorter section of the control groove 922', similar to the first, longer section of the control groove 922' including the slope 9222', has a second stop 9224', on which the actuating element 65', when the cover 92' is pushed back after a progress of the pulling-off process of the cover 92', can come into contact with the main body 91 and thus reliably prevent the actuating element 65' from moving back from this point on. If the pulling-off process of the cover 92' from the main body 91 is executed again, the actuating element 65' leaves, for example assisted by a ramp or the like, the second section of the control groove 922', and the main body 91 subsequently completely leaves the cover 92', in order to release the opening of the injection device covered by a seal, so that the reconstituted substance to be dispensed by the injection device can be ejected.

Preferred embodiments of the present disclosure have been described above, wherein the present disclosure is not limited to the preferred embodiments described above, however. Various modifications in design can be made without departing from the disclosure as specified within the scope of the following claims.

This application claims the priority of European patent application EP 18 174 940.9, the claimed subjects and processes of which are listed below for the sake of completeness:

Subject 1: Device for dispensing at least one substance, in particular to a patient, comprising a first container containing a first substance having a first piston having a first piston rod, wherein the first container is movably arranged in the device, a second container containing a second substance, having a second piston having a second piston rod, wherein the second container is movably arranged in the device, an injection device, and a conduit device for guiding the contents of the second container to the first container and the contents of the first container to the injection device, wherein the first and the second piston are each movable via at least one pre-tensioned spring element, wherein a free end of the first piston rod and a free end of the second piston rod are releasably held by a common holding component, and wherein the common holding component is designed such that a movement of the common holding component results in successive release of the first piston rod and the second piston rod.

Subject 2: Device according to subject 1, wherein the common holding component, which is preferably essentially plate-shaped, holds back the first piston rod and the second piston rod against the pre-tension of the respective pre-tensioned spring element.

Subject 3: Device according to one of the preceding subjects 1 and 2, wherein the common holding component has at least one recess for the free end of the first piston rod and at least one recess for the free end of the second piston rod, the free end of the first piston rod and the free end of the second piston rod each have a depression which is releasably engaged with the common holding component, and a size of the free end of the first and second piston rod and a size of the respective recess and/or a depth of the respective depression is selected such that the free ends of the first and the second piston rod interact differently with the common holding component.

Subject 4: Device according to subject 3, wherein the recess in the common holding component for the free end of the piston rod essentially has a triangular shape and the recess in the common holding component for the free end of the second piston rod essentially has a semicircular shape, and the free end of the first piston rod essentially has a triangular shape and the free end of the second piston rod essentially has a semicircular shape, and/or the depth of the depression in the free end of the second piston rod is deeper than the depth of the depression in the free end of the first piston rod.

Subject 5: Device according to one of the preceding subjects 1 to 4, wherein the at least one pre-tensioned spring element of the first piston moves the first piston together with the first container in relation to the device after the first piston rod is released, and the at least one pre-tensioned spring element of the second piston moves the second piston together with the second container in relation to the device and then moves the second piston in relation to the second container after the second piston rod is released.

Subject 6: Device according to one of the preceding claims 1 to 5, wherein the first substance is different from the second substance.

Subject 7: Device according to one of the preceding subjects 1 to 6, wherein the second substance is a liquid, preferably wherein the liquid is transferred into the first container by moving the second piston toward a container end of the second container, the liquid mixing there with the first substance and this forming a solution, and wherein the solution in the first container can be dispensed via the injection device by moving the first piston toward a container end of the first container.

Subject 8: Device according to subject 7, wherein the first substance is a solid, in particular a lyophilizate.

Subject 9: Device according to one of the preceding subjects 1 to 8, wherein the release of the free end of the first piston rod establishes a fluid connection between the conduit device and the first container due to the corresponding spring element, and wherein a subsequent release of the free end of the second piston rod establishes a fluid connection between the conduit device and the second container due to the corresponding spring element and additionally causes a transfer of the second substance from the second container via the conduit device into the first container.

Subject 10: Device according to one of the preceding subjects 1 to 9, wherein a longitudinal axis of the common holding component is arranged essentially perpendicular to the longitudinal axes of the first and the second piston rod, and wherein a movement direction of the common holding component is preferably substantially perpendicular to the movement directions of the two piston rods.

Subject 11: Device according to one of the preceding subjects 1 to 10, wherein the device furthermore has an activation component which is in mechanical operative connection with the common holding component, and wherein a movement of the activation component results in the movement of the common holding component, preferably wherein a longitudinal axis of the activation component is arranged essentially perpendicular to the longitudinal axis of the common holding component, and wherein a movement direction of the activation component preferably extends essentially perpendicular to the movement direction of the common holding component.

Subject 12: Device according to one of the preceding subjects 1 to 12, wherein the conduit device has a first connection element for a fluid connection with the first container and a second connection element for a fluid connection with the second container, and wherein each connection element is preferably embodied as a needle-like projection to penetrate a septum of the respective container.

Subject 13: Device according to one of the preceding subjects 1 to 12, wherein the conduit device has a fluid connection to the injection device, and/or where the conduit device preferably has a valve element, more preferably a one-way valve, in particular a check valve.

Subject 14: Device according to any one of the preceding subjects 1 to 13, wherein the first container has a first container end and a second container end, and the second container has a first container end and a second container end, wherein the first and second pistons are displaceable between the respective first container end and the respective second container end, and wherein contents of the first container can be dispensed via the injection device by moving the first piston toward the first container end of the first container.

Subject 15: Device according to one of the preceding subjects 1 to 14, wherein each container is cylindrical, and/or the second container is arranged in parallel, in particular in the same direction as the first container in the device.

Subject 16: Method for dispensing at least one substance, in particular to a patient, using a device according to one of the preceding claims, comprising a step of moving the activation component, which is operatively connected to the common holding component, along its longitudinal axis, whereby the common holding component is essentially is moved in the longitudinal direction, in particular perpendicular to the movement direction of the activation component, and in this case first releases the engagement between the common holding component and the free end of the first piston rod and then the engagement between the common holding component and the free end of the second piston rod, preferably wherein the release of the free end of the first piston rod due to the corresponding spring element establishes a fluid connection between the conduit device and the first container, and the subsequent release of the free end of the second piston rod due to the corresponding spring element establishes a fluid connection between the conduit device and the second container and then the second substance is transferred from the second container via the conduit device into the first container.

Subject 17: Method according to subject 16, wherein the first substance is a solid, in particular a lyophilizate, and the second substance is a liquid, and wherein the liquid is transferred into the first container by moving the second piston towards the first end of the second container, the liquid combines with the solid there and this forms a solution, and wherein the solution in the first container is dispensed via the injection device by moving the first piston towards the first container end of the first container.

The invention claimed is:
1. A device for dispensing at least one substance, in particular to a patient, comprising
   a first container containing a first substance having a first piston having a first piston rod,
   a second container containing a second substance having a second piston having a second piston rod,
   an injection device, and a conduit device for guiding the contents of the second container to the first container and the contents of the first container to the injection device, wherein the first and the second container are movably arranged in the device for establishing a fluid connection via a respective connection element with the conduit device, wherein the first and the second piston are each movable via at least one pre-tensioned spring element, wherein a free end of the first piston rod and a free end of the second piston rod are releasably held by a common holding component, and wherein the common holding component is designed such that a movement of the common holding component results in a successive release of the first piston rod and the second piston rod and a movement of the first piston rod and the second piston rod essentially perpendicular to the direction of movement of the common holding component.

2. The device according to claim 1, wherein the common holding component holds the first piston rod and the second piston rod against the pre-tension of the respective pre-tensioned spring element.

3. The device according to claim 1, wherein the common holding component has at least one recess for the free end of the first piston rod and at least one recess for the free end of the second piston rod, the free end of the first piston rod and the free end of the second piston rod each have a depression which is releasably engaged with the common holding component, and at least one of: i) a size of the free end of the first and the second piston rod, ii) a size of the respective recess, or iii) a depth of the respective depression is selected such that the free ends of the first and second piston rods interact differently with the common holding component.

4. The device according to claim 3, wherein the recess in the common holding component for the free end of the first piston rod essentially has a triangular shape and the recess in the common holding component for the free end of the second piston rod essentially has a semicircular shape, and the free end of the first piston rod essentially has a triangular shape and the free end of the second piston rod essentially has a semicircular shape, or the depth of the depression in the free end of the second piston rod is deeper than the depth of the depression in the free end of the first piston rod.

5. The device according to claim 1, wherein the at least one pre-tensioned spring element of the first piston moves the first piston together with the first container in relation to the device after the first piston rod is released, and the at least one pre-tensioned spring element of the second piston moves the second piston together with the second container in relation to the device and then moves the second piston relative to the second container after the second piston rod is released.

6. The device according to claim 1, wherein the first substance is different from the second substance.

7. The device according to claim 1, wherein the second substance is a liquid, wherein the liquid is transferred into the first container by displacing the second piston toward a container end of the second container, the liquid mixes there with the first substance and this forms a solution, and wherein the solution in the first container can be dispensed via the injection device by moving the first piston toward a container end of the first container.

8. The device according to claim 7, wherein the first substance is a solid.

9. The device according to claim 8, wherein the first substance is a lyophilizate.

10. The device according to claim 1, wherein the release of the free end of the first piston rod establishes a fluid connection between the conduit device and the first container due to the corresponding spring element, and wherein a subsequent release of the free end of the second piston rod establishes a fluid connection between the conduit device and the second container due to the corresponding spring element and additionally causes a transfer of the second substance from the second container via the conduit device into the first container.

11. The device according to claim 1, wherein a longitudinal axis of the common holding component is arranged essentially perpendicular to the longitudinal axes of the first and second piston rods.

12. The device according to claim 1, wherein the device furthermore has an activation component which is in mechanical operative connection with the common holding component, and wherein a movement of the activation component results in the movement of the common holding component, wherein a longitudinal axis of the activation component is arranged essentially perpendicular to the longitudinal axis of the common holding component, and wherein a movement direction of the activation component extends essentially perpendicular to the movement direction of the common holding component.

13. The device according to claim 1, wherein the conduit device has a first connection element for fluid connection with the first container and a second connection element for fluid connection with the second container, and wherein each connection element is embodied as a needle-like projection for penetrating a septum of the respective container.

14. The device according to claim 1, wherein the conduit device has a fluid connection to the injection device.

15. The device according to claim 1, wherein the first container has a first container end and a second container end, and the second container has a first container end and a second container end, wherein the first and the second piston are displaceable between the respective first container end and the respective second container end, and wherein contents of the first container can be dispensed via the injection device by displacing the first piston toward the first container end of the first container.

16. The device according to claim 1, wherein each container is cylindrical.

17. The device according to claim 1, wherein the second container is arranged parallel to the first container in the device.

18. A method for dispensing at least one substance using the device according to claim 1, comprising a step of moving the activation component, which is operatively connected to the common holding component, along its longitudinal axis, whereby the common holding component is moved essentially in the longitudinal direction thereof, in particular perpendicular to the movement direction of the activation component, and in this case first releases the engagement between the common holding component and the free end of the first piston rod and then the engagement between the common holding component and the free end of the second piston rod, wherein the release of the free end of the first piston rod due to the corresponding spring element establishes a fluid connection between the conduit device and the first container and the subsequent release of the free end of the second piston rod due to the corresponding spring element establishes a fluid connection between the conduit device and the second container and then the second substance is transferred from the second container via the conduit device into the first container.

19. The method according to claim 18, wherein the first substance is a lyophilizate, and the second substance is a liquid, and wherein by displacing the second piston toward the first container end of the second container, the liquid is transferred into the first container, the liquid combining there with the solid and this forming a solution, and wherein the solution in the first container is dispensed via the injection device by displacing the first piston toward the first container end of the first container.

20. The device according to claim 1, wherein the common holding component is essentially plate-shaped.

21. The device according to claim 1, wherein the conduit device has a valve element.

22. The device according to claim 21, wherein the valve element comprises a one-way valve or a check valve.

23. A device for dispensing a medicament comprising:
   a main body;
   a first container containing a first medicament having a first piston having a first piston rod mounted within the main body along a first longitudinal axis;
   a second container containing a second medicament having a second piston having a second piston rod, where the second container is mounted in the main body along a second longitudinal axis that is parallel to the first longitudinal axis; and
   a first conduit in fluid communication with the first medicament and a second conduit in fluid communication with the second medicament when the first container and the second container are moved axially relative to the main body; and
   a check valve in fluid communication with the first and second conduits,
   wherein the first and the second containers are moved axially a pre-tensioned spring element,
   wherein a free end of the first piston rod and a free end of the second piston rod are releasably held by a common holding component, and
   wherein the common holding component is configured to cause successive release of the first piston rod and the second piston rod when the common holding element moves perpendicular to the direction of movement of the first and second piston rods.

24. The device according to claim 23 further comprising an activation component operatively connected the common holding component such that a movement of the activation component results in the movement of the common holding component, where the movement of the activation component is perpendicular to a longitudinal axis of the common holding component and parallel to the first longitudinal axis and to the second longitudinal axis.

* * * * *